(12) United States Patent
Coqueron et al.

(10) Patent No.: US 9,212,152 B2
(45) Date of Patent: Dec. 15, 2015

(54) PROCESS FOR THE PREPARATION OF N-HYDROXY-1-(1-ALKYL-1H-TETRAZOL-5-YL)-1-PHENYLMETHANIMINE DERIVATIVES

(71) Applicants: Pierre-Yves Coqueron, Lyons (FR); Christophe Dubost, Charbonnieres-les-Bains (FR); Mark Ford, Schmitten (DE); Anne-Sophie Rebstock, Lyons (FR)

(72) Inventors: Pierre-Yves Coqueron, Lyons (FR); Christophe Dubost, Charbonnieres-les-Bains (FR); Mark Ford, Schmitten (DE); Anne-Sophie Rebstock, Lyons (FR)

(73) Assignee: BAYER INTELLECTUAL PROPERTY GMBH (DE)

( * ) Notice: Subject to any disclaimer, the term of this patent is extended or adjusted under 35 U.S.C. 154(b) by 0 days.

(21) Appl. No.: 14/376,931

(22) PCT Filed: Feb. 6, 2013

(86) PCT No.: PCT/EP2013/052309
§ 371 (c)(1),
(2) Date: Aug. 6, 2014

(87) PCT Pub. No.: WO2013/117582
PCT Pub. Date: Aug. 15, 2013

(65) Prior Publication Data
US 2015/0299145 A1    Oct. 22, 2015

Related U.S. Application Data

(60) Provisional application No. 61/607,051, filed on Mar. 6, 2012.

(30) Foreign Application Priority Data

Feb. 9, 2012    (EP) .................... 12356002

(51) Int. Cl.
*C07D 257/04*    (2006.01)

(52) U.S. Cl.
CPC .................... *C07D 257/04* (2013.01)

(58) Field of Classification Search
CPC ...................................... C07D 257/04
See application file for complete search history.

(56) References Cited

U.S. PATENT DOCUMENTS

| 2005/0070439 | A1 | 3/2005 | Kobori et al. ............... 504/261 |
| 2007/0105926 | A1 | 5/2007 | Kobori et al. ............... 514/381 |
| 2012/0004420 | A1 | 1/2012 | Suzumi et al. ............... 548/252 |
| 2012/0330027 | A1 | 12/2012 | Caillon-Morisseau et al. ............... 548/253 |

FOREIGN PATENT DOCUMENTS

| EP | 1426371 A1 | 6/2004 |
| EP | 2407461 A1 | 1/2012 |
| WO | WO 2011/110651 | 9/2011 |

OTHER PUBLICATIONS

International Search Report mailed Mar. 11, 2013 in International Application No. PCT/EP2013/052309.
Richard N. Loeppky et al.: "A Diazonium Ion Cascade from the Nitrosation of Tolazoline, An Imidazoline-Containing Drug", Chemical Research in Toxicology, vol. 21, No. 2, Feb. 1, 2008, pp. 295-307, XP55024615, ISSN: 0893-228X, DOI: 10.1021/tx700317g.

*Primary Examiner* — Rebecca Anderson
*Assistant Examiner* — Karen Cheng
(74) *Attorney, Agent, or Firm* — Ostrolenk Faber LLP

(57) ABSTRACT

The present invention relates to a process for the preparation of N-hydroxy-1-(1-alkyl-1H-tetrazol-5-yl)-1-phenylmethanimine derivatives of the general formula (I)

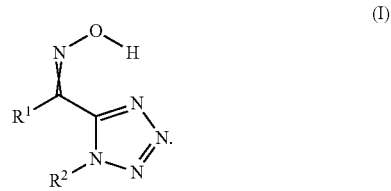

7 Claims, No Drawings

PROCESS FOR THE PREPARATION OF N-HYDROXY-1-(1-ALKYL-1H-TETRAZOL-5-YL)-1-PHENYLMETHANIMINE DERIVATIVES

CROSS-REFERENCE TO RELATED APPLICATION(S)

The present application is a 35 U.S.C. §371 national phase conversion of PCT/EP2013/052309 filed on Feb. 6, 2013, which claims priority of European Application No. 12356002.1 filed on Feb. 9, 2012 and U.S. Provisional Application No. 61/607,051 filed on Mar. 6, 2012. Applicants claim priority to each of the foregoing applications. The PCT International Application was published in the English language.

The present invention relates to a process for the preparation of N-hydroxy-1-(1-alkyl-1H-tetrazol-5-yl)-1-phenyl-methanimine derivatives. N-hydroxy-1-(1-alkyl-1H-tetrazol-5-yl)-1-phenylmethanimine derivatives are important intermediate compounds in active ingredient manufacture or are already fungicidally effective compounds (see e.g. WO 2010/000841 or EP1426371). It is already known that N-hydroxy-1-(1-alkyl-1H-tetrazol-5-yl)-1-phenylmethanimine can be prepared by condensation of hydroxylamines derivatives on (1-methyl-1H-tetrazol-5-yl)(phenyl)methanone (cf. EP2407461, EP1426371 and WO2010/103783). However, the starting material, namely (1-methyl-1H-tetrazol-5-yl)(phenyl)methanone derivatives have to be synthesized after a multi-step sequence or by using a methylisocyanide (cf WO2011/110651) which is a toxic and malodorant reagent and which would cause a problem of hygiene management on industrial scale.

The nitrosation of benzyl heterocylic derivatives is a process only described in two references in the literature (cf Chemical Research in Toxicology, 21(2), 295-307; 2008 and Heterocyclic Communications, 8(6), 613-616; 2002). It proceeds through the use of sodium nitrite, which in acidic medium, is spontaneously converted to a nitronium species, which than reacts on the benzyl heterocyclic derivative. Unfortunately, this reaction fails when applied to 5-benzyl-1-methyl-1H-tetrazole derivatives, which are easily accessible and in good yields from the corresponding N-methyl-2-phenylacetamide derivatives, as described in Tetrahedron Letters (2010), 51(10), 1404-1406. Whilst the use of strong bases at low temperature, such as lithium diisopropyl amide at −78° C., would be expected to yield the corresponding anion of 5-benzyl-1-methyl-1H-tetrazole derivatives and undergo the subsequent nitrosation upon reaction with a nitrite ester, such conditions are not appropriate for a technical synthesis. The problem therefore remained to find a mild; technically feasible synthesis of N-hydroxy-1-(1-alkyl-1H-tetrazol-5-yl)-1-phenylmethanimines starting from the readily available 5-benzyl-1-methyl-1H-tetrazole derivatives. The expected pkA of bezylic protons of aforementioned 5-benzyl-1-methyl-1H-tetrazole derivatives should be comprised between 23 and 25, thus precluding the use of milder, more technically-orientated bases.

Surprisingly, a process to give N-hydroxy-1-(1-alkyl-1H-tetrazol-5-yl)-1-phenylmethanimine derivatives has now been found which overcomes the aforementioned disadvantages.

The invention therefore provides a process for the preparation of N-hydroxy-1-(1-alkyl-1H-tetrazol-5-yl)-1-phenylmethanimine derivatives of the general formula (I)

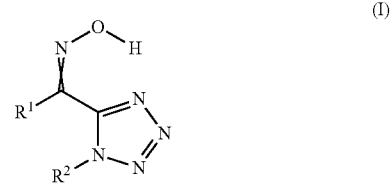

in which $R^1$ is phenyl optionally monosubstituted by halogen, cyano, nitro, $C_1$-$C_8$-alkyl, $C_1$-$C_8$-alkoxy, methylsulphonyl, trifluoromethyl or aryl, $R^2$ is $C_1$-$C_{12}$-alkyl or $C_1$-$C_{12}$-haloalkyl, characterized in that (1) in a first step, 5-benzyl-1-methyl-1H-tetrazoles of the general formula (II)

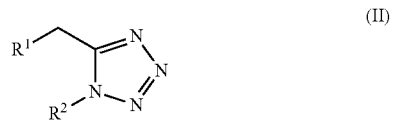

in which $R^1$ and $R^2$ have the meanings given above, are reacted with a nitrite derivative of the general formula (II)

in which $R^3$ is a $C_1$-$C_{12}$-alkyl in the presence of base with a pKa below 20.

In the context of the invention, formula (I)

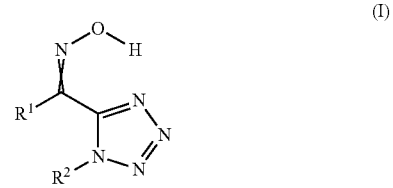

means that the geometry of the compounds of formula (I) can be (E), (Z) or a mixture of both.

The process according to the invention can be illustrated by the following scheme:

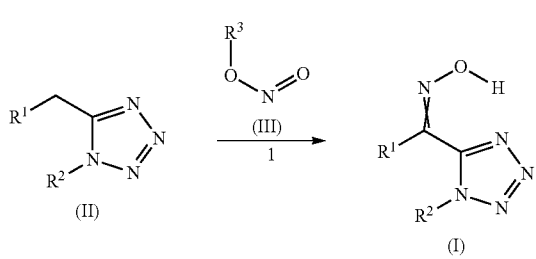

The 5-benzyl-1-methyl-1H-tetrazoles used as starting materials when carrying out the process according to the invention are generally defined by the formula (II).

$R^1$ is preferably phenyl optionally monosubstituted by fluorine, chlorine, bromine, iodine, cyano, nitro, $C_1$-$C_6$-alkyl, methylsulphonyl, trifluoromethyl or phenyl or naphthyl.

$R^1$ is particularly preferably phenyl optionally monosubstituted by fluorine, chlorine, $C_1$-$C_4$-alkyl or $C_1$-$C_3$-alkoxy.

$R^1$ is very particularly preferably phenyl optionally monosubstituted by fluorine, chlorine, methyl, t-butyl, methoxy or ethoxy.

$R^1$ is especially preferably unsubstituted phenyl.

$R^2$ is preferably $C_1$-$C_8$-alkyl or $C_1$-$C_8$-haloalkyl.

$R^2$ is particularly preferably $C_1$-$C_4$-alkyl or $C_1$-$C_4$-haloalkyl.

$R^2$ is very particularly preferably methyl, ethyl, trifluoromethyl.

$R^2$ is especially preferably methyl.

$R^3$ is preferably a $C_1$-$C_4$-alkyl 5-benzyl-1-methyl-1H-tetrazoles of the formula (II) are known, e.g. commercially available, or can be prepared by known processes (cf. Tetrahedron Letters (2010), 51(10), 1404-1406).

The compounds of the formulae (I) may be present as well as salts, N-oxides, metallic complexes and metalloidic complexes thereof or either in pure form or else as mixtures of different possible isomeric forms, in particular of stereoisomers, such as E and Z, threo and erythro, and also optical isomers, such as R and S isomers or atropisomers, but in some cases also of tautomers. Both the E and also the Z isomers, and also the threo and erythro, and the optical isomers, any desired mixtures of these isomers, and the possible tautomeric forms are encompassed by this application. In particular, the possibility of E or Z isomers on the double bond of the oxime group may be mentioned.

In the definitions of the symbols given in the formulae above, collective terms have been used which generally representatively stand for the following substituents:

Halogen stands for fluorine, chlorine, bromine or iodine.

A heteroatom can be nitrogen, oxygen or sulphur.

Unless stated otherwise, a group or a substituted radical can be substituted by one or more of the following groups or atoms, where, in the case of multiple substitution, the substituents may be identical or different: halogen, nitro, hydroxy, cyano, amino, sulphenyl, pentafluoro-•⁶-sulphenyl, formyl, carbaldehyde-O—($C_1$-$C_8$-alkyl) oxime, formyloxy, formylamino, carbamoyl, N-hydroxycarbamoyl, formylamino, (hydroxyimino)-$C_1$-$C_6$-alkyl, $C_1$-$C_8$-alkyl, tri($C_1$-$C_8$-alkyl)silyl, tri($C_1$-$C_8$-alkyl)silyl-$C_1$-$C_8$-alkyl, $C_3$-$C_8$-cycloalkyl, tri($C_1$-$C_8$-alkyl)silyl-$C_3$-$C_8$-cycloalkyl, $C_1$-$C_8$-haloalkyl having 1 to 5 halogen atoms, $C_3$-$C_8$-halocycloalkyl having 1 to 5 halogen atoms, $C_2$-$C_8$-alkenyl, $C_3$-$C_8$-cycloalkenyl, $C_2$-$C_8$-alkynyl, $C_2$-$C_8$-alkenyloxy, $C_2$-$C_8$-alkynyloxy, $C_1$-$C_8$-alkylamino, di-$C_1$-$C_8$-alkylamino, $C_1$-$C_8$-alkoxy, $C_1$-$C_8$-haloalkoxy having 1 to 5 halogen atoms, $C_1$-$C_8$-alkylsulphenyl, $C_1$-$C_8$-halonalkylsulphenyl having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms, $C_1$-$C_8$-alkylcarbonyl, $C_1$-$C_8$-haloalkylcarbonyl having 1 to 5 halogen atoms, $C_1$-$C_8$-alkylcarbamoyl, di-$C_1$-$C_8$-alkylcarbamoyl, N—$C_1$-$C_8$-alkyloxycarbamoyl, $C_1$-$C_8$-alkoxycarbamoyl, N—$C_1$-$C_8$-alkyl-$C_1$-$C_8$-alkoxycarbamoyl, $C_1$-$C_8$-alkoxycarbonyl, $C_1$-$C_8$-haloalkoxycarbonyl having 1 to 5 halogen atoms, $C_1$-$C_8$-alkylcarbonyloxy, $C_1$-$C_8$-haloalkylcarbonyloxy having 1 to 5 halogen atoms, $C_1$-$C_8$-alkylcarbonylamino, $C_1$-$C_8$-haloalkylcarbonylamino having 1 to 5 halogen atoms, $C_1$-$C_8$-alkoxycarbonylamino, $C_1$-$C_8$-haloalkoxycarbonylamino having 1 to 5 halogen atoms, $C_1$-$C_8$-alkylaminocarbonyloxy, di-$C_1$-$C_8$-alkylaminocarbonyloxy, $C_1$-$C_8$-alkyloxycarbonyloxy, $C_1$-$C_8$-alkylsulphenyl, $C_1$-$C_8$-haloalkylsulphenyl having 1 to 5 halogen atoms, $C_1$-$C_8$-alkylsulphynyl, $C_1$-$C_8$-haloalkylsulphynyl having 1 to 5 halogen atoms, $C_1$-$C_8$-alkylsulphonyl, $C_1$-$C_8$-haloalkylsulphonyl having 1 to 5 halogen atoms, $C_1$-$C_8$-alkylaminosulphamoyl, di-$C_1$-$C_8$-alkylaminosulphamoyl, ($C_1$-$C_6$-alkoxyimino)-$C_1$-$C_6$-alkyl, ($C_1$-$C_6$-alkenyloxyimino)-$C_1$-$C_6$-alkyl, ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-haloalkoxyalkyl having 1 to 5 halogen atoms, aryl, heterocyclyl, benzyloxy, benzylsulphenyl, benzylamino, phenoxy, phenylsulphenyl or phenylamino.

Aryl is phenyl or naphthyl.

The first reaction step (1) preferably takes place in the presence of a base when $R^3$ is a $C_1$-$C_{12}$-alkyl. Suitable bases are organic and inorganic bases which are usually used in such reactions. Preference is given to using bases which are selected from but not limited to, for example, the group consisting of hydroxides, alcoholates, acetates, fluorides, phosphates, carbonates and hydrogencarbonates of alkali metal or alkaline earth metals and tertiary amines, such as, but not limited to, trimethylamine, triethylamine, tributylamine, N,N-dimethylaniline, N,N-dimethylbenzylamine, pyridine, alkylpyridines, such as 2-methyl-5-ethylpyridine, N-methylpiperidine, N-methylpyrrolidone, N,N-dimethylaminopyridine, diazabicyclooctane (DABCO), diazabicyclononene (DBN) and diazabicycloundecene (DBU), or mixtures thereof. Particular preference is given here to sodium methanolate, potassium-tert-butanolate, potassium carbonate, potassium hydroxide and sodium hydroxide. Particularly preferred is sodium hydroxide or potassium hydroxide.

The molar ratio of base to the compound of the formula (II) used is for example 0.8-10, preferably 0.9-6, particularly preferably 1.0-3. The use of larger amounts of base is possible in principle, but does not lead to any preferred embodiment and is disadvantageous for reasons of cost.

For the reaction according to the invention, the solvents preferably used are aromatic and/or aliphatic hydrocarbons, amides, nitriles, ethers, in particular toluene, acetonitrile, THF, methylene chloride, or mixtures thereof.

The process according to the invention can generally be carried out in vacuo, at atmospheric pressure or at superatmospheric pressure.

The process according to the invention in step (1) takes place at temperatures of −80 to +100° C., preferably at temperatures of −10 to +25° C.

The present invention is illustrated in more detail by reference to the examples below, without thereby limiting the invention thereto.

PREPARATION EXAMPLES

Example 1

Preparation of sodium {[(1-methyl-1H-tetrazol-5-yl)(phenyl)methylene]amino}oxidanide To a suspension of sodium hydroxyde (115 mg, 2.9 mmol) in 1.5 mL ethanol was added 460 mg of 5-benzyl-1-methyl-1H-tetrazole (2.6 mmol). The mixture was stirred 15 min at room temperature. A solution of isoamylnitrite (353 mg, 3 mmol) in 1 mL ethanol was then added dropwise and the mixture was stirred at room temperature for 3 h. Diethyl ether (5 mL) was then added and the resulting precipitate was filtered and washed with cooled diethyl ether. The white solid was dried under reduced pressure to afford 175 mg of the sodium salt of N-hydroxy-1-(1-methyl-1H-tetrazol-5-yl)-1-phenylmethanimine.

$^1$H-NMR (300 MHz, DMSO): d=7.43 (d, 2H), 7.20 (t, 2H), 7.06 (t, 1H), 3.82 (s, 3H) ppm; log P (pH 2.7): 1.45; MS (ESI): 204.1 ([M+H]$^+$)

Example 2

Preparation of N-hydroxy-1-(1-methyl-1H-tetrazol-5-yl)-1-phenylmethanimine

To a suspension of sodium hydroxyde (115 mg, 2.9 mmol) in 1.5 mL ethanol was added 500 mg of 5-benzyl-1-methyl-1H-tetrazole (2.9 mmol). The mixture was stirred 15 min at room temperature. A solution of isoamylnitrite (353 mg, 3 mmol) in 1 mL ethanol was then added dropwise and the mixture was stirred at room temperature for 16 h. Ether and water were then added and the layers were separated. The aqueous phase was washed with ether and then acidified with HCl 0.1M. The resulting neutral solution was extracted 3 times with ethyl acetate. The organic layers were combined, dried over magnesium sulfate and concentrated to afford 272 mg of the title compound (Z:E mixture) as a white solid.

$^1$H-NMR (400 MHz, DMSO, water signal at δ=1.56; for the sake of simplicity, only the signals of the main diastereoisomer were shown): δ=12.88 (s, 1H), 7.52 (m, 5H), 4.06 (s, 3H)

The invention claimed is:

1. Process for the preparation of N-hydroxy-1-(1-alkyl-1H-tetrazol-5-yl)-1-phenylmethanimine derivatives of the general formula (I)

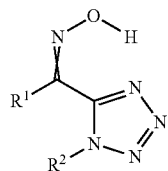

(I)

in which

R$^1$ is phenyl optionally monosubstituted by halogen, cyano, nitro, C$_1$-C$_8$-alkyl, C$_1$-C$_8$-alkoxy, methylsulphonyl, trifluoromethyl or aryl, R$^2$ is C$_1$-C$_{12}$-alkyl or C$_1$-C$_{12}$-haloalkyl, characterized in that (1) in a first step, 5-benzyl-1-methyl-1H-tetrazoles of the general formula (II)

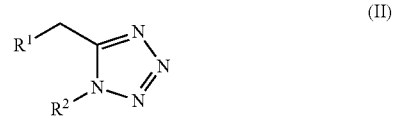

(II)

in which R$^1$ and R$^2$ have the meanings given above, are reacted with a nitrite derivative of the general formula (III)

(III)

in which

R$^3$ is a C$_1$-C$_{12}$-alkyl in the presence of base with a pKa below 20.

2. Process according to claim 1, characterized in that 5-benzyl-1-methyl-1H-tetrazoles of formula (II) are used in which R$^1$ is phenyl optionally monosubstituted by fluorine, chlorine, bromine, iodine, cyano, nitro, C$_1$-C$_6$-alkyl, methylsulphonyl, trifluoromethyl or phenyl or naphthyl;

R$^2$ is C$_1$-C$_8$-alkyl or C$_1$-C$_8$-haloalkyl;

R$^3$ is C$_1$-C$_4$-alkyl.

3. Process according to claim 1 wherein the molar ratio of base to the compound of the formula (II) used is 0.8-10.

4. Process according to claim 1 wherein the base is selected from the list consisting of hydroxides, alcoholates, acetates, fluorides, phosphates, carbonates and hydrogencarbonates of alkali metal or alkaline earth metals and tertiary amines.

5. Process according to claim 1 wherein the base is selected from the list consisting of sodium methanolate, potassium-tert-butanolate, potassium carbonate, potassium hydroxide and sodium hydroxide.

6. Process according to claim 1 wherein the base is selected from the list consisting of sodium hydroxide and potassium hydroxide.

7. Process according to claim 1 wherein step (1) is carried out in a solvent.

* * * * *